United States Patent [19]

Graffunder

[11] Patent Number: 5,391,353

[45] Date of Patent: Feb. 21, 1995

[54] METERING DEVICE WITH RADIAL ARRANGEMENT OF VALVES

[75] Inventor: Horst Graffunder, Berlin, Germany

[73] Assignee: WITA GmbH, Technologiezentrum Teltow, Teltow, Germany

[21] Appl. No.: 949,238

[22] PCT Filed: Apr. 23, 1991

[86] PCT No.: PCT/DE91/00333

§ 371 Date: Nov. 5, 1992

§ 102(e) Date: Nov. 5, 1992

[87] PCT Pub. No.: WO91/17420

PCT Pub. Date: Nov. 14, 1991

[30] Foreign Application Priority Data

May 7, 1990 [DE] Germany .............. 4014602

[51] Int. Cl.$^6$ .............................................. G01N 1/00
[52] U.S. Cl. ................................. 422/103; 422/100; 137/885; 137/625.12; 137/625.15; 251/61.1
[58] Field of Search ................ 422/100, 103, 104; 137/625.12, 625.15, 885; 251/61.1

[56] References Cited

U.S. PATENT DOCUMENTS

| 3,202,180 | 2/1963 | Gray | 137/625.15 |
|---|---|---|---|
| 3,782,682 | 1/1974 | Lale | 251/61.1 |
| 4,633,904 | 1/1987 | Schumann et al. | 137/625.15 |
| 4,702,889 | 10/1987 | Cabrera et al. | 422/103 |
| 4,722,830 | 2/1988 | Urie et al. | 422/81 |

FOREIGN PATENT DOCUMENTS

| 76451 | 4/1983 | European Pat. Off. | 137/625.15 |
|---|---|---|---|
| 79535 | 5/1983 | European Pat. Off. | 137/625.15 |
| 8300721 | 9/1984 | Netherlands | 422/103 |
| 9009595 | 8/1990 | WIPO | 422/103 |

Primary Examiner—Robert J. Warden
Assistant Examiner—Hien Tran
Attorney, Agent, or Firm—Brooks Haidt Haffner & Delahunty

[57] ABSTRACT

A multi-function metering device having a plurality of control valves arranged on an annular support. Each control valve can be controlled independently of the others. The annular arrangement of the valves allows the lines to be kept short so that the metering device is particularly suitable for micro-scale work such as in a sequenator or a synthesis machine for the production of nucleotides or peptides.

4 Claims, 5 Drawing Sheets

METERING DEVICE WITH RADIAL ARRANGEMENT OF VALVES

In laboratory technology one frequently encounters the problem that certain substances in the form of gases or liquids must be metered, i.e. a given quantity of said substance must be dispensed. Particularly in the analytical field, for instance upon the carrying out of tests, different reagents must be introduced into reaction vessels one after the other. Since reagents must very frequently be introduced in identical quantity into a large number of reaction vessels, an automated sample dispenser or multi-distributor is advantageous.

Upon the analytical separation of mixtures, the eluate coming for instance from a separating column is separated into individual fractions by means of fraction collectors.

These fields of use require a metering device which operates automatically and reliably.

It is the object of the present invention to make available a metering device which has a plurality of control valves, it being possible to control each valve independently of the other valves. There is to be made available, in particular, a metering device, which is suitable for use in a sequenator for the analysis of proteins and peptides.

The object of the present invention is a metering device which is free of dead volume and which has a plurality of pneumatically controllable valves and is characterized by the fact that the valves are arranged substantially in a circle on an annular support.

In one preferred embodiment, the annular support encloses an essentially circular hollow space.

Particularly upon the use as metering device in a sequenator or in a synthesis machine for the production of nucleotides or peptides, this geometric arrangement affords the advantage that one or more reaction vessels can be arranged in the circular hollow space. The individual feed lines from the control valves to the reaction vessels can be kept very short due to the radial arrangement.

In the case of a sequenator, the reactor and the converter can be located within the circular hollow space. For an explanation of the problems which occur upon the automatic sequencing of proteins and peptides which are present in only very small quantities, reference is had to the general article by B. Wittmann-Liebold "Advanced automatic microsequencing of proteins and peptides, Modern Methods in Protein Chemistry"—Review Articles, (1983), Walter de Gryter & Co., Berlin, N. Y.

In one preferred embodiment, the metering device of the invention consists of a first ring which has screw connections and assures mechanical stability. This first ring can consist of several individual structural parts. Thus, for instance, the first ring can consist of an upper and a lower ring which are connected via an intermediate ring by means of fasteners. This first ring assures the mechanical stability of the metering device and is therefore preferably made of metal. Particularly preferred materials are stainless high-grade steel and aluminum.

Furthermore, the metering device of the invention has a second ring which is made of a chemically inert material. There enter into consideration for this quartz or a copolymer known as KelF made from vinylidene fluoride and chlortrifluorethylene. Other synthetic materials also enter into consideration, provided they have the required mechanical strength and the required resistance to the chemical reagents with which the material can come into contact. The selection of the most suitable material of course always depends on the reagents with which the metering device of the invention comes into contact. Between the first and the second ring there is arranged a diaphragm consisting of a chemically inert material.

The first ring will, as a rule, be constructed in such a manner that the second ring is held by it, the second ring being pressed against the upper part of the first ring.

In the case of the metering device according to the invention, a pneumatically controllable valve is formed in the manner that the first ring has a hole in its upper part which hole extends perpendicularly to the diameter of the ring from the surface of the upper part of the first ring to the lower surface of said part. At the lower side of this first ring said hole opens into a dome-shaped depression. There is concerned a recess in the lower side of the first ring which has the shape of a spherical segment. Its radius of depth preferably corresponds to twice the diameter of the diaphragm arranged between first and second ring. If, for instance, the diaphragm has a thickness of 0.25 mm, then the dome should have a depth of 0.5 mm.

The surface of the second ring opposite the dome-shaped structure has at least two holes. These holes extend through the second ring and can debouch either at the bottom side or on the inner side of the second ring. One of the holes serves in this connection as a feed line for the metered material and the other hole serves as a discharge line for same.

A pneumatically controllable valve, which is used in the metering device of the invention, contains the holes in the second ring which form the feed line and the discharge line for the metered material. In closed condition of the valve, the diaphragm provided between the first and the second ring is pressed against the second ring. The feed and discharge lines are thereby closed. The pressing pressure is created by a pressure which is conducted through the hole in the upper part of the first ring onto the diaphragm. When the valve is opened, the diaphragm is lifted off from the second ring, whereby a connection is created between feed line and discharge line. The lifting off of the diaphragm from the second ring is effected in the manner that a vacuum is applied in the hole through the upper part of the first ring.

Whether a vacuum or pressure is applied to the hole through the first ring is determined by a preferably electronically controlled control element. This electronically controllable control element, which is known per se, is connected to a pressure line and a vacuum line. Depending on the control selected, vacuum or pressure is applied to the hole through the first ring of the metering device and the diaphragm is accordingly pressed against the second ring or else lifted off therefrom.

In one preferred embodiment, the vacuum line and the pressure line are integrated into the first ring. The lines represent circular channels inside the first ring of the metering device of the invention. These circularly arranged pressure lines have connecting lines to the controllable control units. In this way, pressure or vacuum can be applied via the control element to the diaphragm which leads to a closing or opening of the valve.

Depending on the intended use of the metering device of the invention, the holes in the second ring of the metering device are given a corresponding configuration. If the metering device of the invention is to be used as multi-distributor, one of the holes can be developed as circular groove. This groove represents a channel which extends along the side of the second ring facing the first ring. This groove must in this connection be developed in such a manner that it connects the surfaces which are opposite the dome-shaped structures of the first ring to each other. Said groove can connect several or all of these surfaces of a metering device. In assembled condition, all discharge lines or feed lines of these valves are then connected to a single discharge line or feed line, respectively. In this way, the same material to be metered can be discharged or received via several valves.

There are also conceivable developments of the present invention in which the second ring has several grooves which surround a certain segment of the second ring. As a result, a previously determined group of control valves can be supplied with the same material to be metered.

Since in a preferred embodiment the first and second rings are detachably connected to each other by means of connecting elements, differently configured second rings can be assembled with the first ring. A high flexibility of the metering device of the invention is thus achieved. The second rings used in the specific case can be adapted with respect to the geometry of their feed or discharge lines to the most varied purposes of use.

By the radial arrangement of the feed lines and discharge lines which can lead to a central reaction vessel, for instance a reactor, a collector or derivatizer, short paths are achieved for the feed lines and/or discharge lines.

Due to the shorter paths, shorter times for the meterings are also made possible. Thus, smaller quantities of reagents can be metered and less solvent is required for the cleaning and neutralizing of the central capillaries. The advantage that smaller quantities of metered material need be introduced is of particular importance when tests are to be carried out on a particularly small scale. If, for instance, only a few nanograms of a protein are available, then the sequencing of said protein must be carried out on a microscale. There is required for this an apparatus equipment which permits working with extremely small quantities of reagents. This is made possible by the metering device of the invention.

Another advantage of the metering device of the invention consists in the fact that the reagents come into contact only with chemically inert material. Therefore, chemical damage to the metering device due to aggressive chemicals need not be expected. The seals of the feed lines and discharge lines are high vacuum-tight. The difference of the pressure stability between inlet line and discharge line always amounts to at least 3 bar.

The metering device of the invention can be used for various applications. As multi-distributor, the metering device of the invention can serve to reliably distribute given reagents or chemicals into a plurality of reaction vessels.

Furthermore, the metering device of the invention can also be used as fraction collector. Another possibility of using the metering device of the invention consists in using it as automatic sample dispenser.

BRIEF DESCRIPTION OF THE DRAWINGS

The figures are to explain the preferred embodiments of the present invention.

DETAILED DESCRIPTION OF THE PREFERRED EMBODIMENTS

Figure 1:
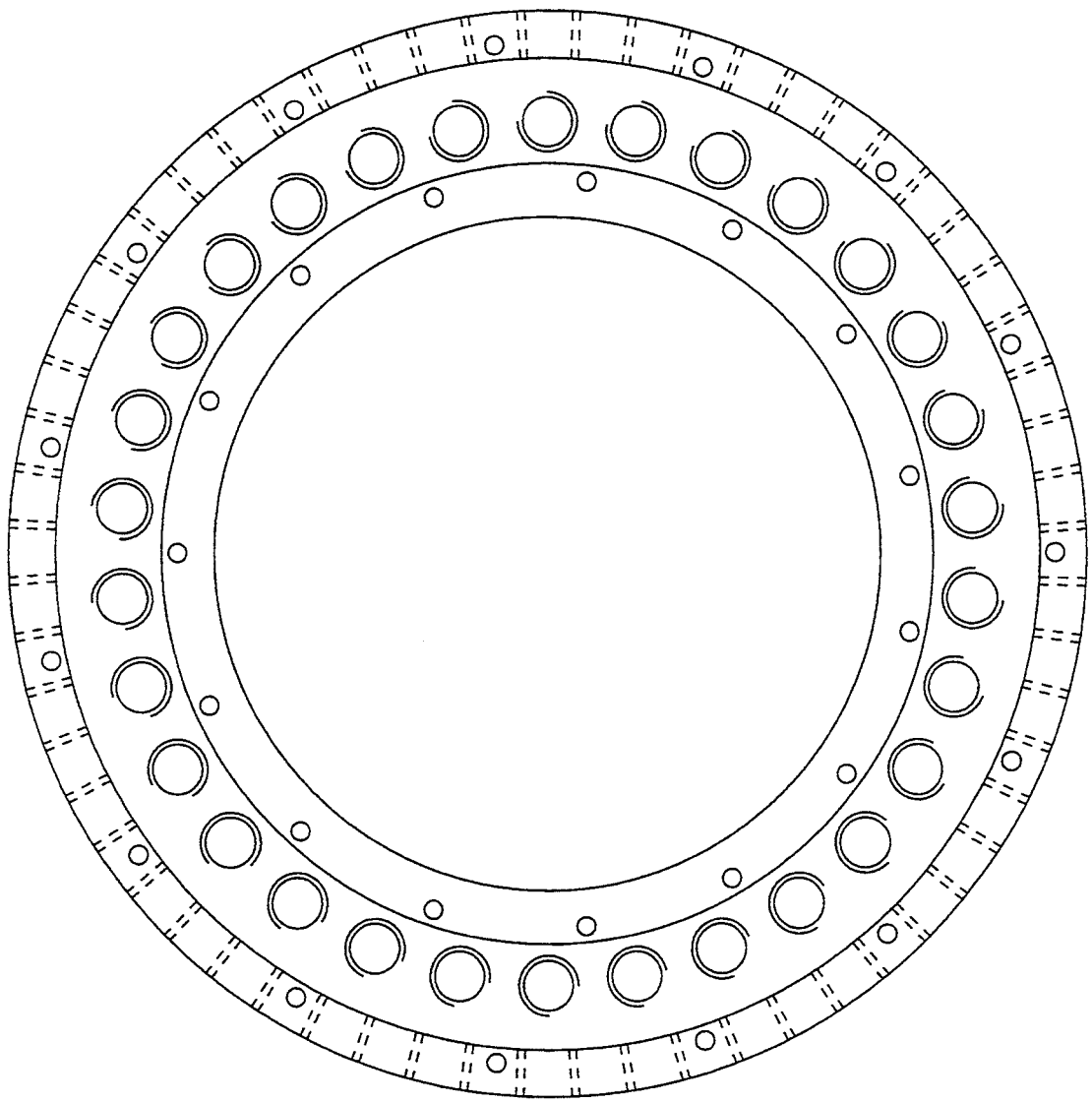
FIG. 1 is a top view of the metering device of the invention.

FIG. 1 is a top view of the metering device of the invention, the electronically controllable control units not being visible. The control valves are arranged in a circle on the annular support which encloses a circular hollow space.

Figure 2:
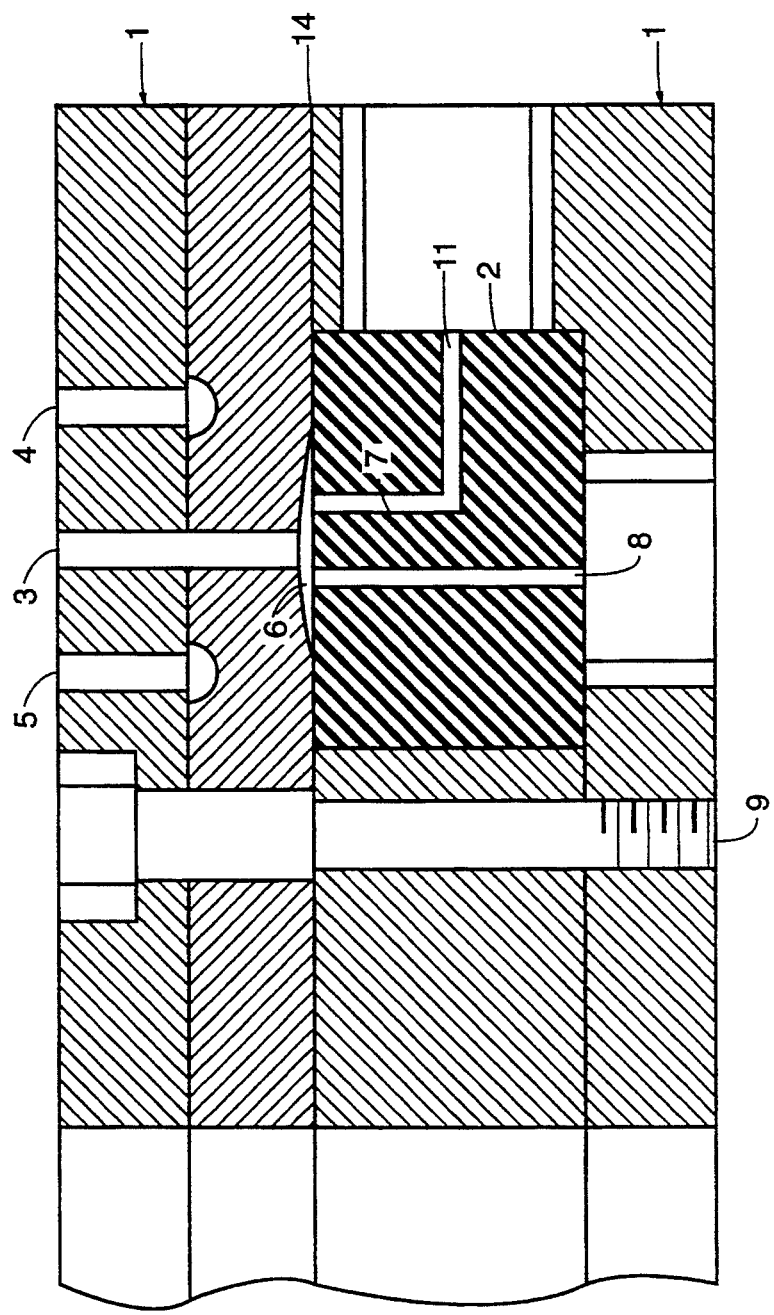
FIG. 2 is a cross section through a valve.

FIG. 2 is a cross section through a valve. Also in this case, the electronically controllable control units are not shown. The first ring is designated (1) and consists of an upper part and a lower part which are connected via a connection part by means of holding elements (9). The second ring (2) has two holes (8) and (11). One of the holes constitutes the discharge line (8) and one the feed line (11). Between the first ring (1) and the second ring (2), there is the diaphragm (14). Above the surface into which the lines (11) and (8) debouch, the upper part of the first ring has a dome-shaped depression (6). Into said dome-shaped depression (6), the hole (3), which extends perpendicular to the diameter of the ring from the upper side of the upper part of the first ring, debouches. The connecting lines (4) and (5) lead to the electronically controllable control element (not shown) and connect the latter to the vacuum or pressure line, respectively, which is arranged in the upper part of the first ring.

Figure 3:
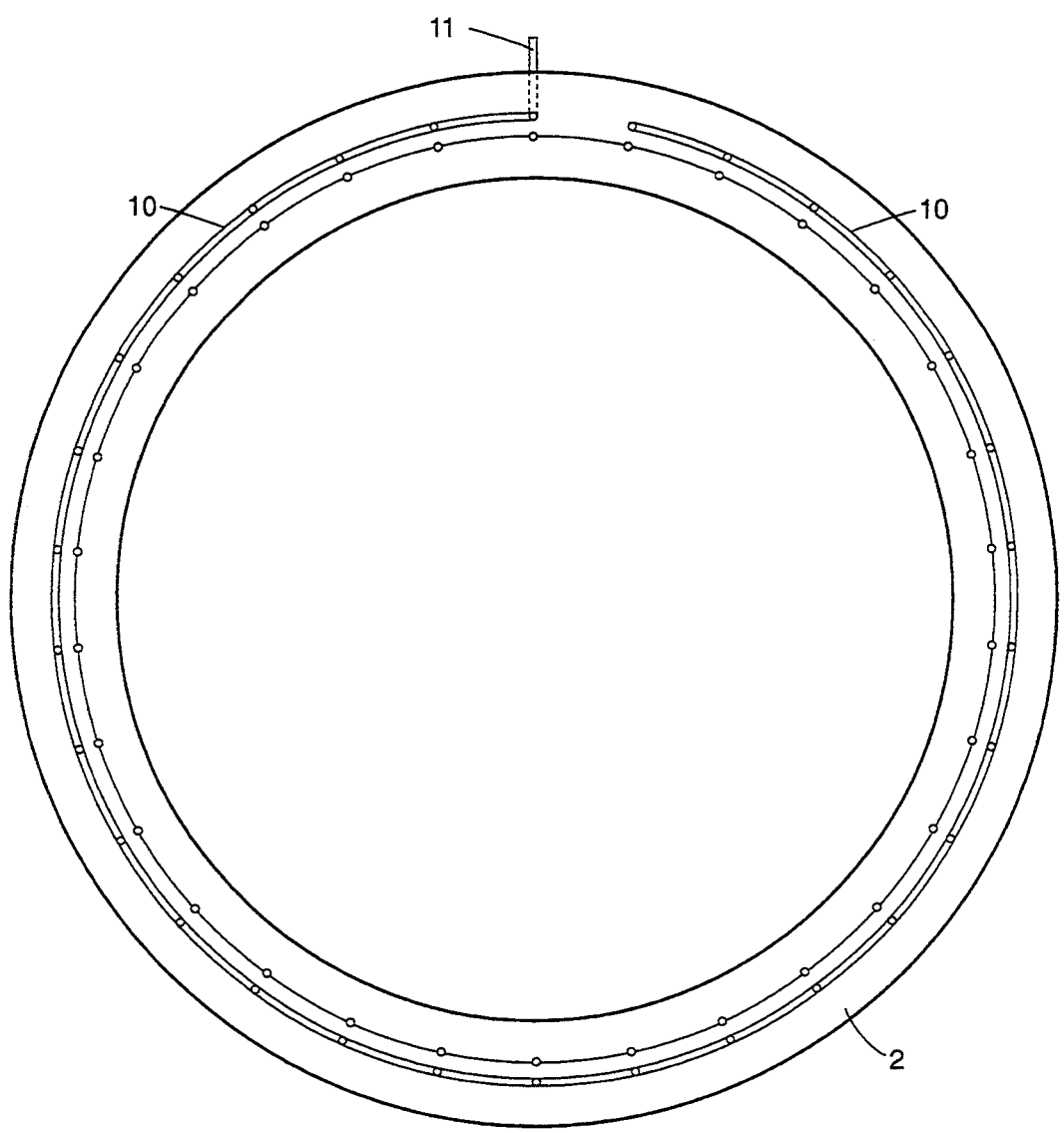
FIG. 3 is a top view of an embodiment of the second ring (2).

FIG. 3 is a top view of an embodiment of the second ring (2). On the upper side of said ring, there extends a groove (10) which connects the individual valves to each other. Via the feed line (11), the material to be metered can be introduced into the groove (10).

Figure 4:
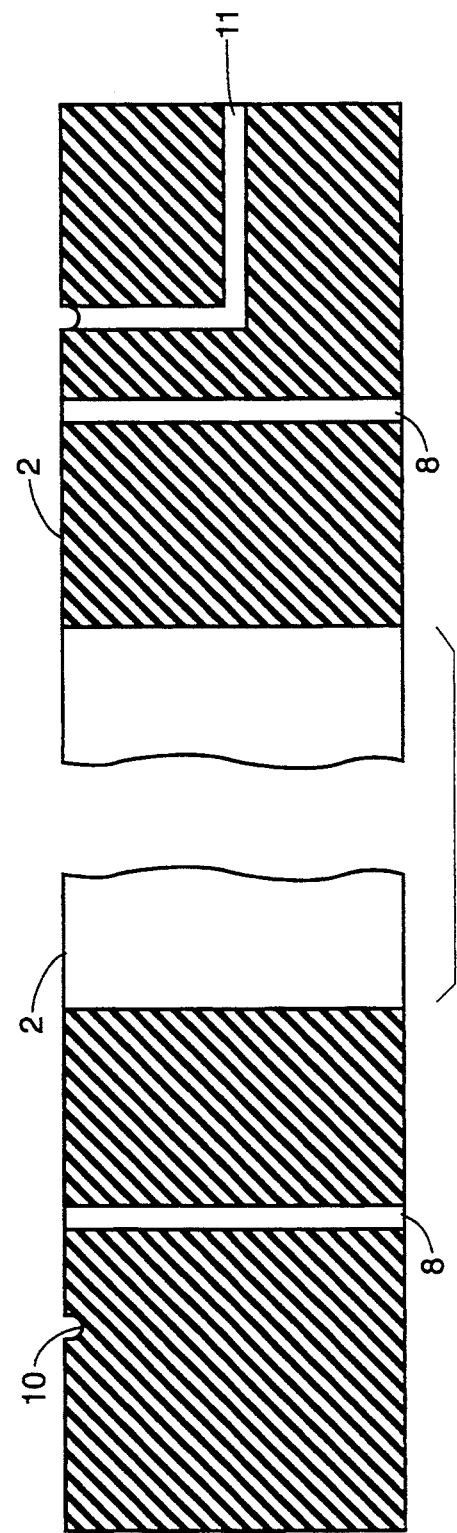
FIG. 4 is a cross section through the second ring (2) shown in FIG. 3.

FIG. 4 is a cross section through the second ring (2) shown in FIG. 3. Through the feed line (11), the entire groove (10) is filled with material to be metered. In the open condition of the valve, the material to be metered can be discharged via the discharge line (8).

Figure 5:
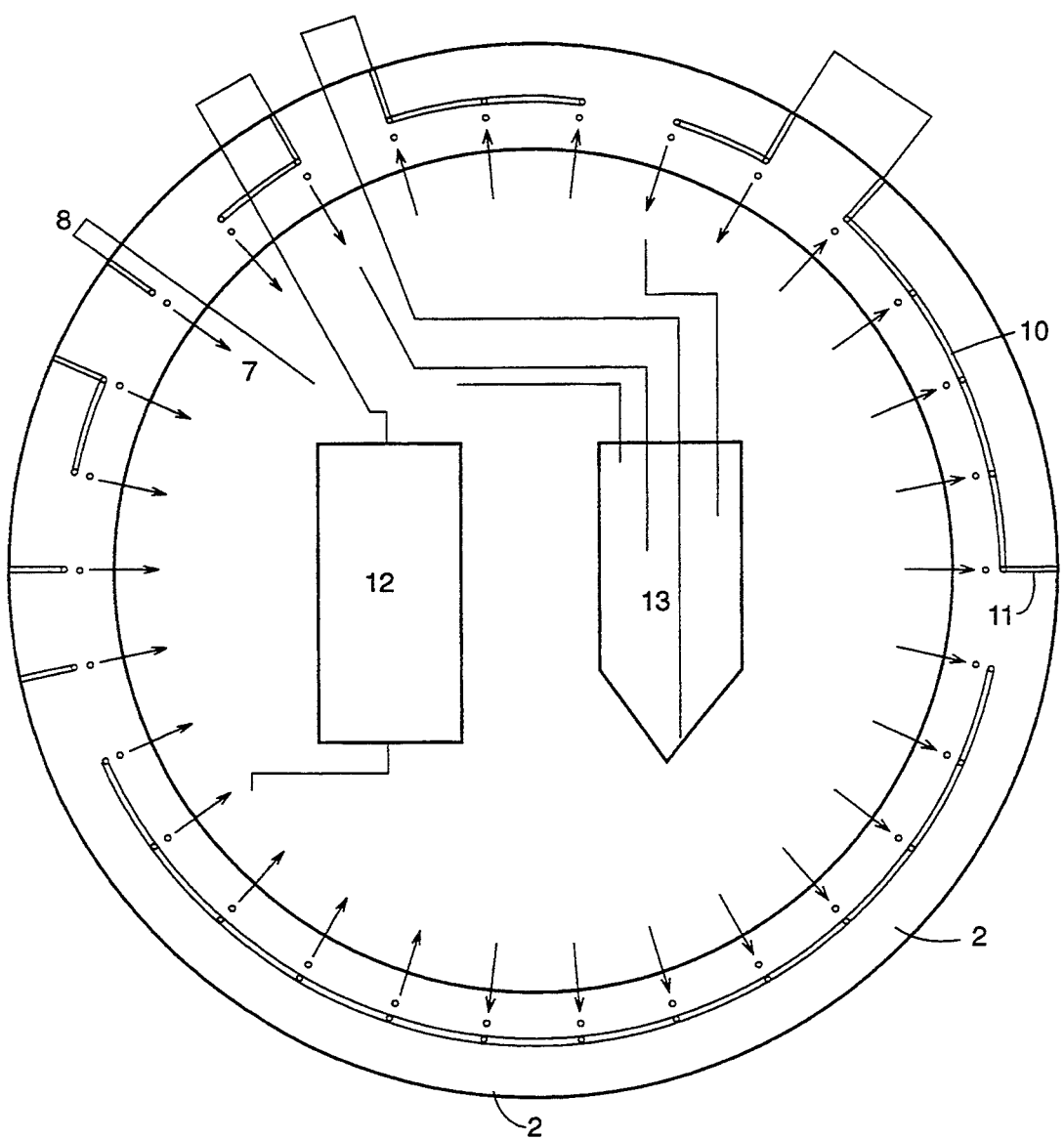
FIG. 5 shows another preferred embodiment of the second ring (2).

FIG. 5 shows another preferred embodiment of the second ring (2). There are shown several grooves (10) which, in each case, connect a given number of valves to each other. A given reagent can be filled into each of the grooves and metered via the valve. The valve can just as well be used in the other direction, namely in the sense that, via the feed line which debouches on the inner wall of the second ring, material to be metered can be introduced which can be discharged via the groove when the valve is open. The second ring of the metering device shown in FIG. 5 is particularly suitable for use in an amino acid sequencing device. Some lines lead for instance into the reactor (12) or into the converter (13).

I claim:

1. A metering device comprising a plurality of independently controllable valves, arranged substantially in a circle on an annular support, the annular support enclosing a substantially circular hollow space and consisting of a first ring and a second ring, the second ring consisting of a chemically inert material, the first ring being secured to the second ring by a holding element, and a diaphragm consisting of a chemically inert material being disposed between the first ring and the second ring, each controllable valve comprising a through-hole radially disposed in the first ring, said hole debouching into a dome-shaped depression, and two through-holes in the second ring debouching opposite the dome-shaped depression, one of the two through-holes of second rise serving as a feed line and the other as a discharge line, wherein the valve is in a closed condition when the diaphragm is pressed against the second ring and the valve is in an open condition when the diaphragm is lifted off the second ring.

2. The metering device of claim 1 wherein the first ring is made of a metal.

3. The metering device of claim 1 wherein one of the two through-holes of the second ring serving as feed line or discharge line is formed by a groove disposed in the second ring said groove connecting each controllable valve.

4. The metering device of claim 1 further comprising a pressure line and a vacuum line disposed in the first ring and in independently controllable pneumatic communication with each through-hole radially disposed in the first ring.

* * * * *